United States Patent [19]

Lee

[11] Patent Number: 5,115,816
[45] Date of Patent: May 26, 1992

[54] SINGLE-HAND CONTROLLED FINE NEEDLE ASPIRATION DEVICE

[75] Inventor: Peter F. Lee, Eden Prairie, Minn.

[73] Assignee: Peter F. Lee, Inc., Edina, Minn.

[21] Appl. No.: 645,568

[22] Filed: Jan. 24, 1991

[51] Int. Cl.⁵ ............................................. A61B 10/00
[52] U.S. Cl. ................................... 128/749; 128/763; 604/187
[58] Field of Search ............... 128/763, 753, 752, 765, 128/758; 604/187, 234, 233, 232, 316

[56] References Cited

U.S. PATENT DOCUMENTS

| | | | |
|---|---|---|---|
| Re. 32,214 | 7/1986 | Schramm | 604/232 |
| 798,093 | 8/1905 | Dean | 604/204 |
| 819,330 | 1/1906 | Ycaza | 604/218 |
| 1,039,591 | 9/1912 | Prideaux | 604/135 |
| 1,718,596 | 6/1929 | Smith | 604/223 |
| 2,198,666 | 4/1940 | Gruskin | 604/117 |
| 2,295,849 | 9/1942 | Kayden | 604/136 |
| 2,472,116 | 6/1949 | Maynes | 604/136 |
| 2,496,111 | 1/1950 | Turkel | 128/754 |
| 2,550,394 | 4/1951 | Young et al. | 604/193 |
| 2,660,342 | 11/1953 | Ruf | 222/340 |
| 2,705,494 | 4/1955 | Broadwin | 604/210 |
| 2,735,427 | 2/1956 | Sullivan | 604/135 |
| 2,854,975 | 10/1958 | Cohen | 604/227 |
| 2,863,452 | 12/1958 | Ogle, Sr. | 604/210 |
| 3,366,103 | 1/1968 | Keller | 128/764 |
| 3,819,091 | 6/1974 | Hollender | 222/327 |
| 3,882,849 | 5/1975 | Jamshidi | 128/753 |
| 3,938,505 | 2/1976 | Jamshidi | 128/753 |
| 4,256,119 | 3/1981 | Gauthier | 128/754 |
| 4,257,425 | 3/1981 | Ryan | 128/758 |
| 4,354,507 | 10/1982 | Raitto | 128/763 |
| 4,401,108 | 8/1983 | Galkin et al. | 600/5 |
| 4,411,653 | 10/1983 | Razi | 604/157 |
| 4,484,915 | 11/1984 | Tartaglia | 604/227 |
| 4,594,073 | 6/1986 | Stine | 604/187 |
| 4,664,128 | 5/1987 | Lee | 128/783 |
| 4,687,472 | 8/1987 | Gross | 604/223 |
| 4,738,664 | 4/1988 | Prindle | 604/228 |
| 4,968,303 | 11/1990 | Clarke et al. | 604/187 |

Primary Examiner—Max Hindenburg
Assistant Examiner—Guy V. Tucker
Attorney, Agent, or Firm—Merchant, Gould, Smith, Edell, Welter & Schmidt

[57] ABSTRACT

An improved disposable single-hand controlled aspirating device for medical aspirating activities most particularly fine needle biopsy procedures. The aspirating device includes a syringe barrel, a plunger operative in the barrel, and a finger grip assembly that is mounted to the syringe barrel and plunger for controlling plunger movement within the barrel. The finger grip assembly includes a body member and a trigger member slidably engaged within the body member. More specifically, the finger grip assembly resembles a pistol-like handle and trigger arrangement that enables a user of the device to control plunger movement in the syringe barrel with a single hand.

7 Claims, 2 Drawing Sheets

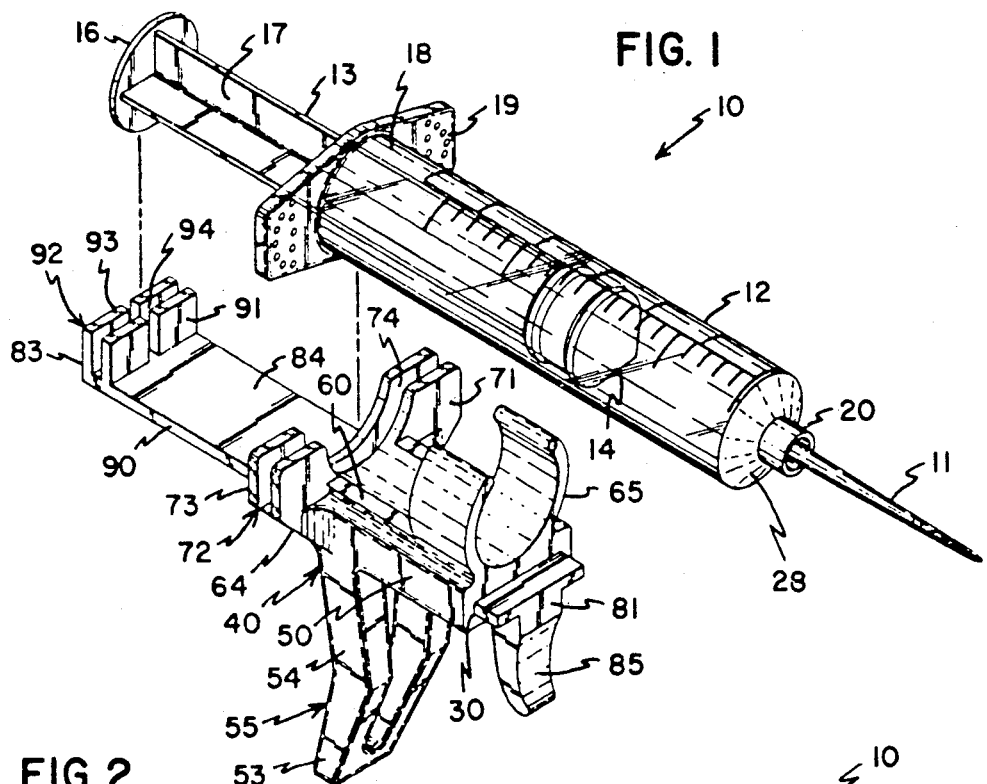
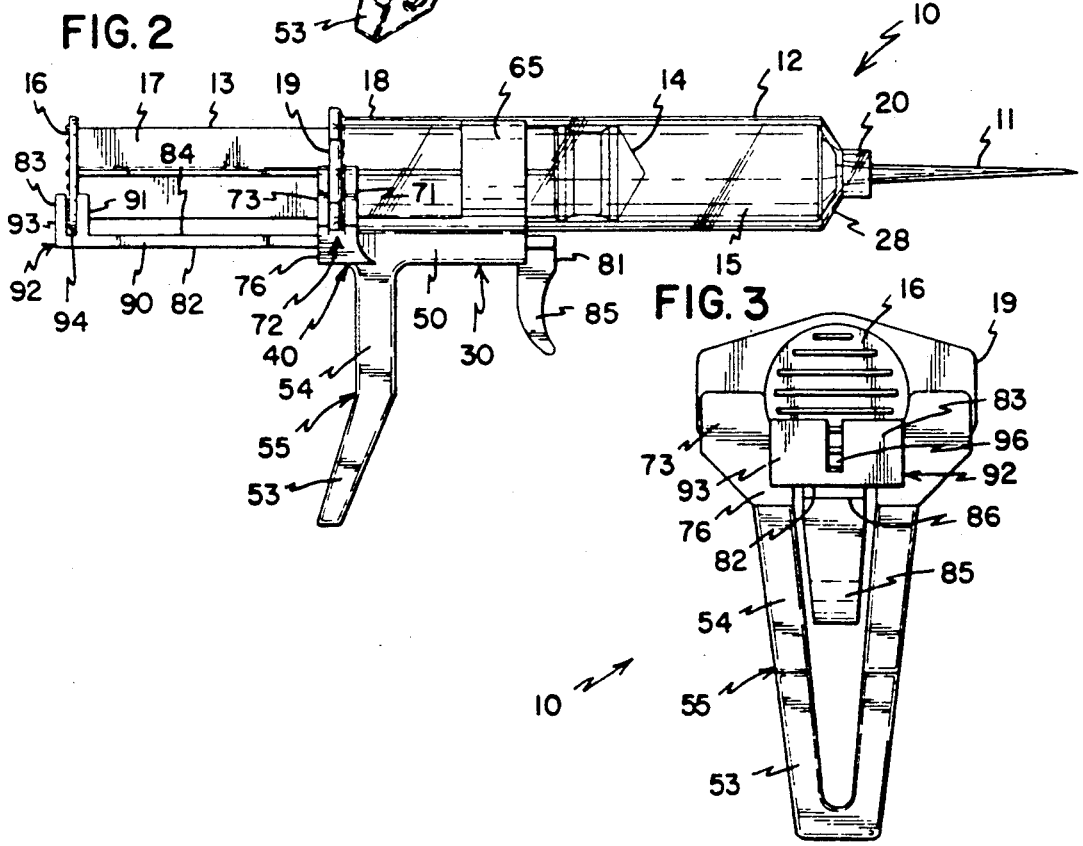

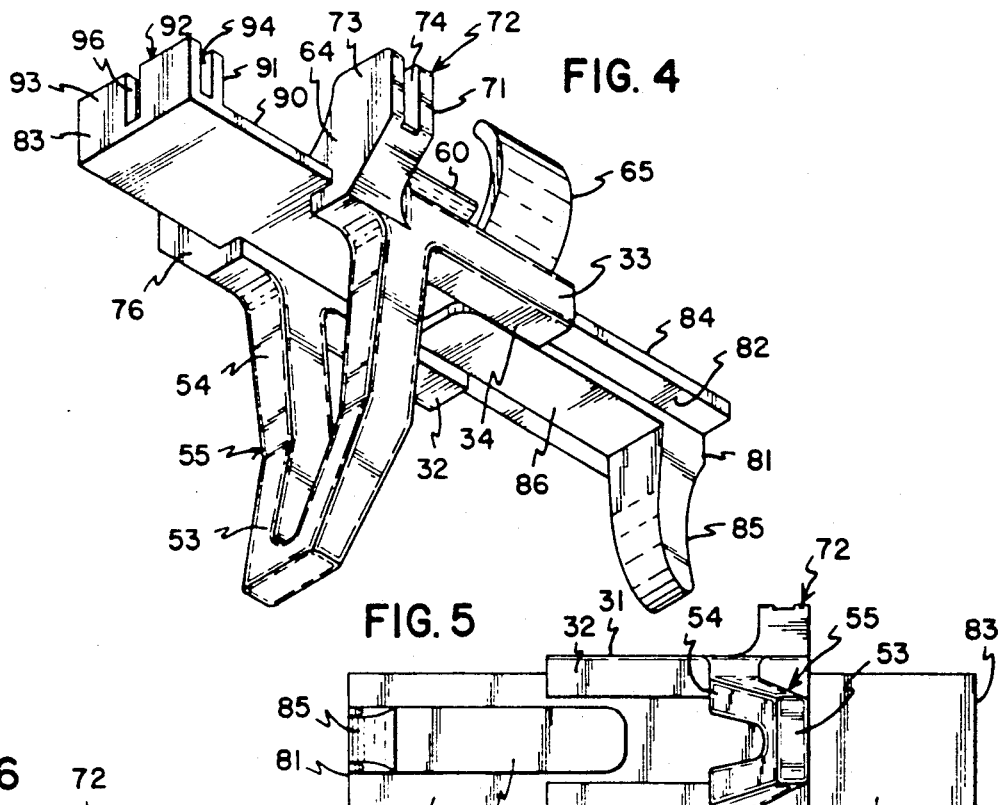
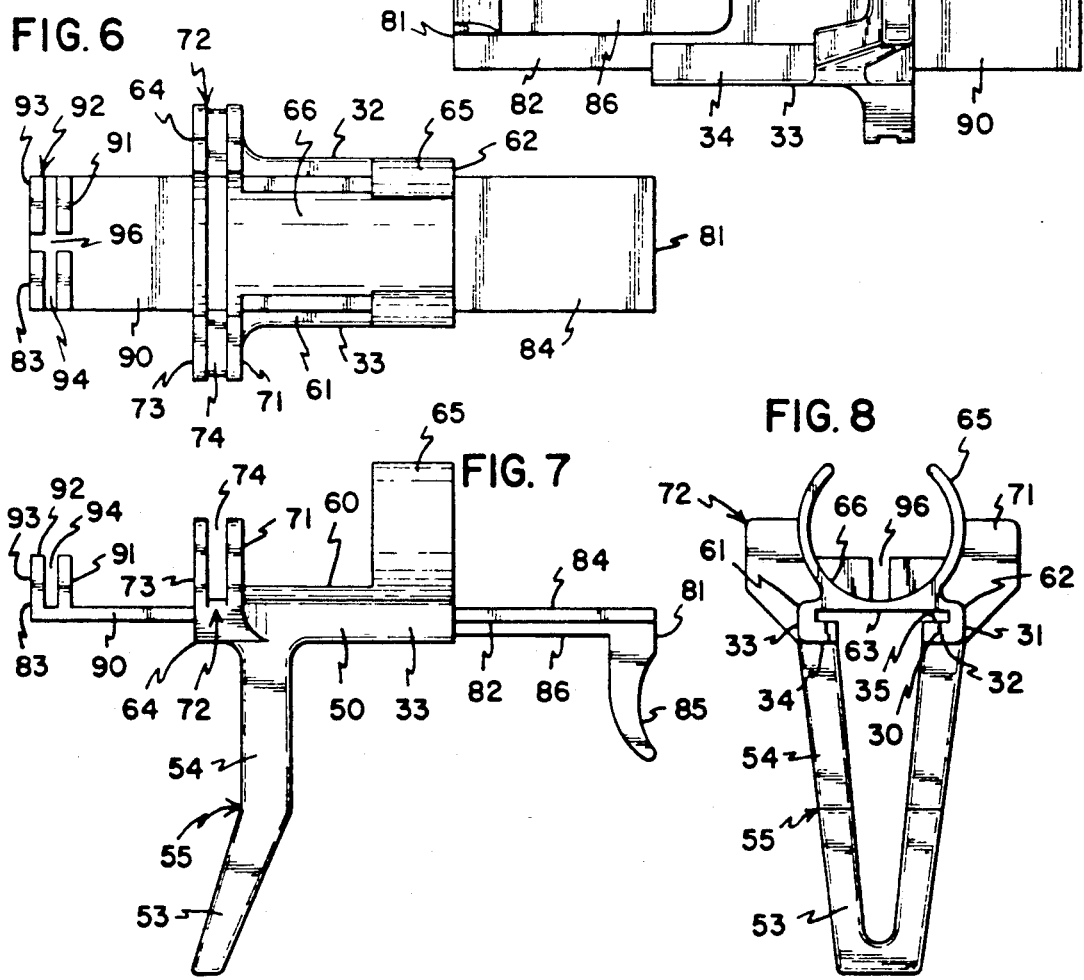

SINGLE-HAND CONTROLLED FINE NEEDLE ASPIRATION DEVICE

TECHNICAL FIELD

The present invention provides an aspirating device that can be controlled by a single-hand during various biopsy procedures, most specifically, fine needle aspiration biopsies of cytologic specimens.

BACKGROUND OF THE INVENTION

In medical applications an aspiration device is one which applies suction or partial vacuum to draw a fluid or sample into a syringe or into an attached needle lumen. Such devices are particularly useful for securing specimens from palpable and non-palpable lesions found in the thyroid, breast, lymph nodes, prostate, liver, kidney, lung and pancreas for histologic and cytologic examination.

The simplest and most widely used prior art aspirating device is a conventional, plastic hypodermic syringe of the type having a hollow needle opening into a syringe barrel and a plunger for varying the volume and pressure inside the barrel. In use, negative pressure is created by drawing back o the plunger. This required two hands, one to hold the syringe barrel and one to withdraw the plunger. The main disadvantage to using a conventional syringe only as an aspirating device to assist in biopsy, is the necessity to have one hand free to assist in the procedure.

At the present time, biopsy specimens are obtained by surgical excision or by needle biopsy. In needle biopsy, specimens are obtained by any of several techniques, all of which involve applying negative pressure to a syringe with an attached needle.

Where a soft tissue specimen is desired, such as in liver biopsy, continued suction is applied to the needle to assist in severing and retrieving the specimen. This procedure can require two people to perform the biopsy or the use of a syringe device wherein the operator can lock the plunger back in a continuous suction position. (See, e.g., U.S. Pat. Nos. 3,882,849 and 3,938,505 to Jamshidi). One hand control is accomplished, but variable suction is not available or needed for this procedure.

When doing fine or thin needle aspiration biopsy of a nodule, it is necessary to secure or immobilize the mass. This is done with two fingers of one hand, while making multiple sticks with the needle, and at the same time applying suction with the other hand. It is of paramount importance that the operator be able to stop suction and neutralize syringe barrel pressure at precisely the right time.

Prior medical aspiration devices that attempt to provide for single-hand control suffer from disadvantages of being structurally complicated and cumbersome. These are reusable devices that incorporate metal rods, springs and handle assemblies that are coupled to a plastic syringe. These devices place the syringe and attached needle considerably distant from the operator's hand, resulting in potential unsteadiness, and also distant from the patient, resulting in procedure awkwardness and patient anxiety.

In U.S. Pat. No. 4,664,128, a single-hand controlled aspiration device is provided. The device disclosed in U.S. Pat. No. 4,664,128 includes a finger grip member positioned near the proximal end of the syringe and a spring surrounding the external portion of the plunger to bias the plunger outwardly from the syringe barrel. However, due to the outward biasing action of the spring the device is best suited for biopsy procedures other than fine needle aspiration procedures. Since fine needle aspiration with the device described in U.S. Pat. No. 4,664,128 requires specimen collection only in the hub at the distal end of the syringe barrel, the outward biasing of the spring around the plunger unnecessarily complicates control of syringe barrel pressure. Specifically, once a specimen is drawn into the barrel hub a sufficient counterforce must be applied to stop the outward movement of the plunger otherwise, if negative pressure in the barrel is not neutralized, the specimen is aspirated into the syringe handle and artifaction will occur. Alternatively, if the counterforce pressure applied to the plunger is too great the specimen will be prematurely discharged from the syringe barrel.

Accordingly, there is a need for an improved single-hand operated aspiration device for conducting fine needle biopsy procedures.

BRIEF DESCRIPTION OF THE INVENTION

The present invention is an improved aspirating device designed for single-hand operation, especially in fine needle aspiration biopsy procedures. Particularly, the present invention provides a pistol grip assembly and finger tip control for the precise application of negative and positive pressure within the syringe barrel, and to instantly be able to neutralize pressure to an ambient state.

The finger grip assembly forms a component part of the aspirating device including a syringe barrel and a plunger. The finger grip assembly resembles a pistol-like handle and trigger assembly that allows an operator to precisely control equalizing pressure in the syringe while performing biopsy procedures, most specifically fine needle aspiration biopsies. The compact size and structure of the finger grip assembly of the present invention permits the user to be closer to the patient thus improving the biopsy procedure technique.

The syringe barrel includes a proximal end and a distal end. The proximal end includes an outer rim and the distal end is provided with a hub and an opening through the hub. The hub is designed to accommodate a needle which when attached to the hub provides for fluid communication between the syringe barrel of the device and the needle. The plunger is positioned in the barrel for changing the volume and pressure inside the barrel, thereby providing the necessary partial vacuum or negative pressure for aspiration as well as the positive pressure needed for expulsion of fluid.

The finger grip assembly includes a body member and a trigger member slidable within the body member. The body member includes a syringe barrel holder section with an inner end, an outer end, a front surface, a back surface, a single outwardly projecting handle, and a trigger guide section between the handle and the syringe barrel holder section. Preferably, the trigger guide section includes opposing inwardly flanged side walls extending from the back surface of the syringe barrel holder section and defining a trigger member guide channel along the syringe barrel holder section. The trigger guide channel provides for slidable engagement of the trigger member within the body member of the finger grip assembly. In a preferred embodiment, the handle extends outwardly from the trigger guide section and has an opening therein to accommodate trigger member travel through the handle and trigger guide section. One end of the syringe barrel holder section is provided with a syringe barrel securement element in the form of an annular or C-shaped collar. The other end of the syringe barrel holder section is provided with a retaining bracket for the outer rim of the syringe barrel. The trigger member has an inner surface and an outer surface and includes a single flange at one end that extends away from the outer surface in a substantially perpendicular direction a sufficient distance to support at least one finger of a user. The other end of the trigger member includes a plunger withdrawal extension which projects away from the inner surface in a substantially perpendicular direction. The plunger withdrawal extension serves to outwardly direct the plunger from the barrel when a user grips the device with one hand and squeezes the flange toward the handle.

According to the present invention, a disposable aspirating device for fine needle aspiration procedures including a plastic syringe, a plastic plunger, and a plastic finger grip assembly mountable to the syringe and plunger is provided.

A primary purpose of the device is to provide an improved method for conducting biopsy procedures involving fine needle aspiration. The device of the present invention required only one hand to be operated effectively. The other hand is free for palpation or to immobilize the nodule during the biopsy procedure. The device allows precise control of the pressure applied while the needle is being inserted, while the needle is in the material to be sampled, and while the needle is being retracted.

The present invention solves deficiencies found in the prior art. The device is compact in size thereby minimizing the distance from the patient during the biopsy procedure. The device allows an operator to precisely control the application and cessation of suction of the device with one hand during fine needle aspiration procedures while the user's other hand is free to secure a lesion or immobilize a palpable mass. Further, the simplicity of the invention lends itself to production as a disposable item, eliminating the need for costly and time consuming sterilization, maintenance and storage.

The speed with which the present invention may be used can also help minimize artifaction of the sample due to contact with air. Samples may be expelled directly onto slides simply by once again forcing the plunger into the syringe after having obtained the desired sample.

It will be appreciated that the present invention provides an improved aspirating device controllable by a single hand and useful for performing biopsy procedures and particularly fine needle aspiration procedures.

BRIEF DESCRIPTION OF THE DRAWINGS

FIG. 1 is a perspective view of the device embodying the principles of the present invention.

FIG. 2 is a side view of the device embodying the principles of the present invention.

FIG. 3 is a rear view of the device embodying the principles of the present invention.

FIG. 4 is a bottom perspective view of the finger grip assembly of the present invention.

FIG. 5 is a bottom view of the finger grip assembly of the present invention.

FIG. 6 is a top view of the finger grip assembly of the present invention.

FIG. 7 is a side view of the finger grip assembly of the present invention.

FIG. 8 is a front view of the body member of the finger grip assembly of the present invention.

DETAILED DESCRIPTION OF THE INVENTION

A preferred embodiment of the present invention will be explained with reference to FIGS. 1 through 8, in which like elements are designated with like reference numbers.

In a preferred embodiment, an aspirating device 10 is provided and includes a syringe barrel 12, a plunger 13 operative in the barrel 12, and a finger grip assembly 40, that provides control of plunger 13 movement in barrel 12 as described herein. The aspirating device 10 when used in fine needle aspirating procedures will include a thin-walled hollow needle 11, the lumen of which opens through a transparent hub 20 into barrel 12 of the aspirating device 10.

The barrel of the aspirating device 10 has an exterior wall, interior wall, a distal end 28 and a proximal end 18. The walls and ends define a hollow interior space having a predetermined volume. Further, the barrel 12 includes a hub 20, an opening through the hub 20 and barrel 12 at the distal end 28.

The plunger 13 extends within and external to the barrel 12 and is operable therein. Particularly, the plunger 13 has one end inside the barrel 12 and another end external to the barrel 12. The plunger 13 has a gasket 14 at the end inside the barrel 12 which interacts with the walls of the barrel 12 to effectively create a space 15 inside the barrel 12. The gasket 14 consists of material different than the barrel, such as rubber, so that the interior plunger end is sealingly received within the barrel 12. The plunger 13 variably controls the volume and pressure within the barrel space 15. When plunger 13 is positioned in the barrel 12 the only opening into the interior of the barrel is provided by the opening at the distal end 28. When needle 11 is attached at hub 20, the only opening into the barrel 12 is provided by the lumen of needle 11. At the end of the plunger 13, which is outside barrel 12, the plunger 13 is provided with a pressure plate 16.

An important feature of the present invention is a finger grip assembly 40 which is mounted to the exterior wall of barrel 12 by a securement element 65. As seen best in FIGS. 1 and 2, a preferred securement element is an annular or C-shaped collar 65. When mounted to syringe barrel 12 and plunger 13 in the manner shown in FIGS. 1 and 2, finger grip assembly 40 provides precise control of aspirating device 10, thereby facilitating the procedure for obtaining biopsy specimens.

Referring to FIGS. 1-8, finger grip assembly 40, includes a body member 50 and a trigger member 90 which is slidable within channel 35 of trigger guide section 30 of body 50. Body member 50 includes a syringe barrel holder section 60 having an inner end 64, outer end 62, front surface 61, and back surface 63. Body member 50 further includes a single outwardly projecting handle 55. Preferably, handle 55 includes a first section 54 extending perpendicular from trigger guide section 30 and a second section 53 which extends at an obtuse angle from section 54 to facilitate gripping of handle 55 by a user's hand. In the preferred embodiment, syringe barrel holder section 60 includes an integral securement collar 65 at outer end 62. As seen best in FIGS. 1, 2, 4, 6 and 7, inner end 64 is provided with retaining means for outer rim 19 of syringe barrel 12. While the retaining means for outer rim 19 can have a number of configurations, in the preferred embodiment shown, inner end 64 is provided with a bracket 72 shaped to hold outer rim 19. Specifically, bracket 72 includes a front wall 71, back wall 73 and bracket slot 74. It is to be understood that alternate outer rim 19 retaining structures such as grooves or notches at the inner end 64 can be designed by those of skill in the art. As discussed herein, bracket 72 further includes a bracket shoulder 76 best seen in FIGS. 2, 3, 4 and 7. Shoulder 76 extends below the operative engagement area of trigger member 90 in trigger guide section 30.

As best seen in FIG. 8, trigger guide section 30 of body member 50 is formed by a pair of opposing side walls 31, 33, extending from back surface 63 to front surface 61 of body member 50. Side wall 31, 33 include flanged portions 32, 34 which together with side walls 31, 33 define trigger member guide channel 35 along the back surface 63 of syringe barrel holder section 60. As assembled, trigger member 90 is positioned in slidable engagement to body 50 within channel 35 of trigger guide section 30. As best seen in FIGS. 4 and 5, in the preferred embodiment shown, handle 55 extends downwardly from side wall flanges 32, 34 and has an opening 57 therein to accommodate travel of trigger member 90 through the handle 55 and trigger guide section 30. It will be appreciated that channel 35, together with opening 57, not only provide for trigger member 90 movement through the entire length of trigger guide section 30, but also allow for assembly and disassembly of body 50 and trigger member 90.

Trigger member 90 includes first end 81, second end 83, inner surface 84 and outer surface 82. As best seen in FIGS. 1 and 2, first end 81 includes trigger flange 85 which is preferably curved and extends away from outer surface 82 in a substantially perpendicular direction a sufficient distance to support at least one finger of a user's hand. Referring to FIGS. 4 and 5, first end 81 further includes guide member 86 preferred or integral with flange 85 to facilitate linear movement of trigger member 90 within channel 35. Guide member 86 extends along outer surface 82 a distance sufficient to provide support and maximal linear movement of trigger member 90 through channel 35 and the opening or slot 57 in handle 55. In the preferred embodiment, guide member 86 extends along outer surface 82 about one-fourth to one-half of the distance toward second end 83. This distance can be readily adjusted by one skilled in the art. Second end 83 of trigger member 90 is provided with a plunger withdrawal extension 92 which outwardly directs plunger 13 from barrel 12 when apparatus 10 is operated. As seen in FIGS. 1-3, plunger withdrawal extension 92 projects away from inner surface 84 in a substantially perpendicular direction. In a preferred embodiment, plunger withdrawal extension 92 includes a front wall 91, and spaced back wall 93 defining a plunger holding slot 94 therebetween. Securement of plunger pressure plate 16 in slot 94 of plunger withdrawal extension 92 enables plunger 13 to be outwardly directed from barrel 12 when flange 85 is squeezed towards handle 55 by the application of pressure by one hand of the user of device 10. As seen best in FIG. 1, 2, 4 and 6, plunger withdrawal extension 92 can be provided with a perpendicular slot 96 which accommodates an alignment arm 17 of plunger 13; thereby further securing plunger 13 in alignment along the lateral axis of device 10.

To further insure alignment of syringe barrel 12 in the overall aspirating device 10, syringe barrel holder 60 is provided with a curved syringe rest portion 66 along its front surface 61. Additionally, to facilitate proper movement of trigger member 90 in channel 35 of guide 30, bracket shoulder 76 extends downwardly below outer surface 82 a sufficient distance to preclude contact between a user's hand and trigger element 90 as it moves linearly in guide section 30.

As seen best in FIGS. 1 and 2, when aspirating device 10 is assembled, syringe barrel 12 is secured to body 50 along front surface 61 of syringe barrel holder 60 by annular C-shaped clip 65 and with outer rim 19 retained within slot 74 of bracket 72. Pressure plate 16 of plunger 13 is retained in plunger withdrawal extension 92 in slots 94, 96. Withdrawal of plunger 13 from barrel 12 is accomplished by applying fingertip pressure to flange 85 and squeezing flange 85 toward handle 55. The movement of flange 85 toward handle 55 results in plunger withdrawal extension 92 directing plunger 13 outwardly from the syringe barrel 12. To redirect plunger 13 into syringe barrel 12 an operator need merely apply pressure to back wall 93, of plunger withdrawal extension 92, resulting in forward movement of plunger 13 into syringe barrel 12. By way of example, operation of the device in a fine needle aspiration biopsy procedure is described below.

In fine needle aspiration with device 10, a fluid is removed from a subcutaneous mass such as a nodule or a palpable mass. It is necessary for the physician to secure the lesion or immobilize the mass with the fingers of one hand, while the needle is introduced through the skin. Specifically, the area to be biopsied is aseptically cleaned with an alcohol swab. A thin needle of about 22 gauge and two inches in length is attached to hub 20 of the syringe. With one hand, the nodule to be biopsied is held between the thumb and index finger. The aspirating device 10 is preliminarily arranged with the plunger 13 positioned well within barrel 12. Holding the aspirating device the attached needle is inserted into the mass to be biopsied. The plunger 13 of the device 10 is retracted by squeezing the flange 85 with the index finger, creating negative pressure within the syringe barrel 12. The needle is moved back and forth within the mass and redirected, while negative pressure is maintained. As aspirated material enters the hub 20 of the needle, the flange 85 is released. This neutralizes the pressure within the syringe barrel 12 and allows the aspirate in the hub 20 to remain in the hub 20 while the needle is removed. The needle is then withdrawn from the patient and the aspirated fluid promptly expelled directly onto a slide by forcing the plunger 13 downwardly into the barrel by applying pressure to back wall 93. It is important that the user be able to control the application and cessation of suction, since artifaction will occur if the fluid is aspirated into the syringe barrel and exposed to air. The speed of performing fine needle aspiration with the present device 10 minimizes possible artifaction due to exposure to air. A distinct advantage of the device described herein over the prior art is that precise control of the termination of negative pressure during sample removal can be accomplished. The present apparatus eliminates the need for any application of positive pressure to neutralize negative pressure in barrel 12 once the specimen is visible in transparent hub 20;

thereby eliminating the previously described difficulties of performing fine needle aspiration procedures with presently available single-hand controlled aspirating devices.

It should be understood that the above-described embodiment of the present invention is merely exemplary, and that the spirit and scope of the present invention are not limited thereto, being defined by the claims set forth below.

I claim:

1. A disposable aspirating device comprising:
   a. a plastic syringe barrel having an exterior wall, an interior wall, a distal end and a proximal end, said walls and said ends defining a hollow interior space having a predetermined volume, said distal end having an opening extending through a hub, said proximal end terminating at an outer rim;
   b. a plastic plunger operative in said barrel, said plunger extending both within said barrel and external to said barrel proximal end and having an interior end sealingly received inside said barrel and an exterior end outside said barrel, said plunger being movable in said barrel inwardly toward said distal end and outwardly away from said distal end, thereby varying the volume of and pressure within said barrel interior space, said plunger including a pressure plate at said exterior end; and
   c. a plastic finger grip assembly mounted to said syringe barrel and having a body member and a trigger member slidable within said body member, said body member having a syringe barrel holder section with an inner end, an outer end, a front surface and a back surface, a single outwardly projecting handle, and a trigger guide section between said handle and syringe barrel holder section, said trigger guide section includes opposing inwardly flanged side walls extending from said back surface of said syringe barrel holder section and defining a trigger member guide channel along said syringe barrel holder section, said handle extending outwardly from said trigger guide section and having an opening therein to accommodate trigger member travel through said handle and said trigger guide section, said trigger member having an inner surface, an outer surface, a first end and a second end, said trigger member including a single flange proximate said first end and a plunger withdrawal extension proximate said second end, said flange extending away from said outer surface in a substantially perpendicular direction a sufficient distance to support at least one finger of a user and said plunger withdrawal extension projecting away from said inner surface proximate said second end in a substantially perpendicular direction a sufficient distance to engage said plunger pressure plate so as to direct said plunger outwardly from said barrel when said flange is squeezed toward said handle, said trigger member flange further comprising an integral guide member extending along said outer surface toward said second end, said guide member cooperatively engaging said channel to facilitate linear movement of said trigger member in said trigger guide section.

2. The disposable aspirating device of claim 1 wherein said plunger withdrawal extension has a front wall and a back wall defining a pressure plate accommodating slot therebetween.

3. The disposable aspirating device of claim 1 wherein said outer rim of said barrel is secured in a slot defined by a first wall and second wall of a bracket at the inner end of said syringe barrel holder section.

4. The disposable aspirating device of claim 3 wherein said outer end of said syringe barrel holder section is secured to said syringe barrel by a C-shaped clip.

5. The disposable aspirating device of claim 4 wherein said bracket has a shoulder extending a sufficient distance below said guide section to preclude contact between a user's hand and said trigger element when said trigger element is moved within said guide section.

6. A disposable aspirating device comprising:
   a. a plastic syringe barrel having an exterior wall, an interior wall, a distal end and a proximal end, said walls and said ends defining a hollow interior space having a predetermined volume, said distal end having an opening extending through a hub, said proximal end terminating at an outer rim;
   b. a plastic plunger operative in said barrel, said plunger extending both within said barrel and external to said barrel proximal end and having an interior end sealingly received inside said barrel and an exterior end outside said barrel, said plunger being movable in said barrel inwardly toward said distal end and outwardly away from said distal end, thereby varying the volume of and pressure within said barrel interior space, said plunger including a pressure plate at said exterior end; and
   c. a plastic finger grip assembly mounted to said syringe barrel and having a body member and a trigger member slidably engaged within said body member, said body member having a syringe barrel holder section with an inner end, an outer end, a front surface and a back surface, a single outwardly projecting handle and a trigger guide section between said handle and syringe barrel holder section, said trigger guide section including opposing inwardly flanged side walls extending from said back surface of said syringe barrel holder section and defining a trigger member guide channel along said syringe barrel holder section, said handle extending outwardly from said trigger guide section and having an opening therein to accommodate trigger member travel through said handle and said trigger guide section, said syringe barrel securably engaged to said syringe barrel holder section by an integral C-shaped clip projecting from said outer end, and with said outer rim positioned in a slot defined by a front wall and a back wall of a bracket at the inner end of said syringe barrel holder section, said bracket further comprising a shoulder portion extending a sufficient distance below said guide section to preclude contact between a user's hand and said trigger element when said trigger element is moved in said guide section, said trigger member having an inner surface, an outer surface, a first end and a second end, said trigger member including a single flange and guide member proximate said first end, said flange extending away from said outer surface in a substantially perpendicular direction a sufficient distance to support at least one finger of a user, said guide member being integral with and extending from said flange along said outer surface toward said second end, said guide member cooperatively engaging said channel to facilitate linear movement of said trigger member in said trigger guide section, said trigger member further comprising a plunger withdrawal extension proximate said second end, said plunger withdrawal extension projecting away from said inner surface in a substantially perpendicular direction and including a front wall and a back wall defining a pressure plate accommodating slot therebetween, said plunger withdrawal extension outwardly directing said plunger from said barrel when a user applies a force squeezing said flange toward said handle.

7. The disposable aspirating device of claim 6 wherein said plunger withdrawal extension includes a perpendicular slot accommodating an alignment arm of said plunger.

* * * * *